United States Patent [19]
Carroll et al.

[11] Patent Number: 5,846,513
[45] Date of Patent: Dec. 8, 1998

[54] TUMOR LOCALIZATION AND REMOVAL SYSTEM USING PENETRATABLE DETECTION PROBE AND REMOVAL INSTRUMENT

[75] Inventors: Robert G. Carroll, Largo, Fla.; Robin A. Wise, Jr., Morgan Hill, Calif.

[73] Assignee: Carewise Medical Products Corporation, Morgan Hill, Calif.

[21] Appl. No.: 889,469

[22] Filed: Jul. 8, 1997

[51] Int. Cl.$^6$ .............................. G01T 1/161; A61B 6/00; A61K 51/00

[52] U.S. Cl. .................. 424/111; 424/9.1; 250/336.1; 250/363.1; 250/370.01; 128/659

[58] Field of Search ............................... 250/336.1, 363.1, 250/370.01, 370; 128/659; 424/1.11, 9.1

[56] References Cited

U.S. PATENT DOCUMENTS

| | | |
|---|---|---|
| 4,801,803 | 1/1989 | Denen et al. . |
| 4,959,547 | 9/1990 | Carroll et al. . |
| 5,036,201 | 7/1991 | Carroll et al. . |
| 5,119,818 | 6/1992 | Carroll et al. . |
| 5,170,055 | 12/1992 | Carroll et al. . |

OTHER PUBLICATIONS

Wong et al. Int. J. Radiation Oncology Biol. Phys. vol. 14, pp. 353–359, 1988.

*Primary Examiner*—Toni R. Scheiner
*Assistant Examiner*—Lin Sun-Hoffman
*Attorney, Agent, or Firm*—Caesar, Rivise, Bernstein, Cohen & Pokotilow, Ltd.

[57] ABSTRACT

A system for detecting and destroying living tumor tissue within the body of a living being. The system is arranged to be used with a tumor localizing radiopharmaceutical. The system includes a percutaneously insertable radiation detecting probe, an associated analyzer, and a percutaneously insertable tumor removing instrument, e.g., a resectoscope. The radiation detecting probe includes a needle unit having a radiation sensor component therein and a handle to which the needle unit is releasably mounted. The needle is arranged to be inserted through a small percutaneous portal into the patient's body and is movable to various positions within the suspected tumor to detect the presence of radiation indicative of cancerous tissue. The probe can then be removed and the tumor removing instrument inserted through the portal to destroy and/or remove the cancerous tissue. The instrument not only destroys the tagged tissue, but also removes it from the body of the being so that it can be assayed for radiation to confirm that the removed tissue is cancerous and not healthy tissue. A collimator may be used with the probe to establish the probe's field of view.

93 Claims, 3 Drawing Sheets

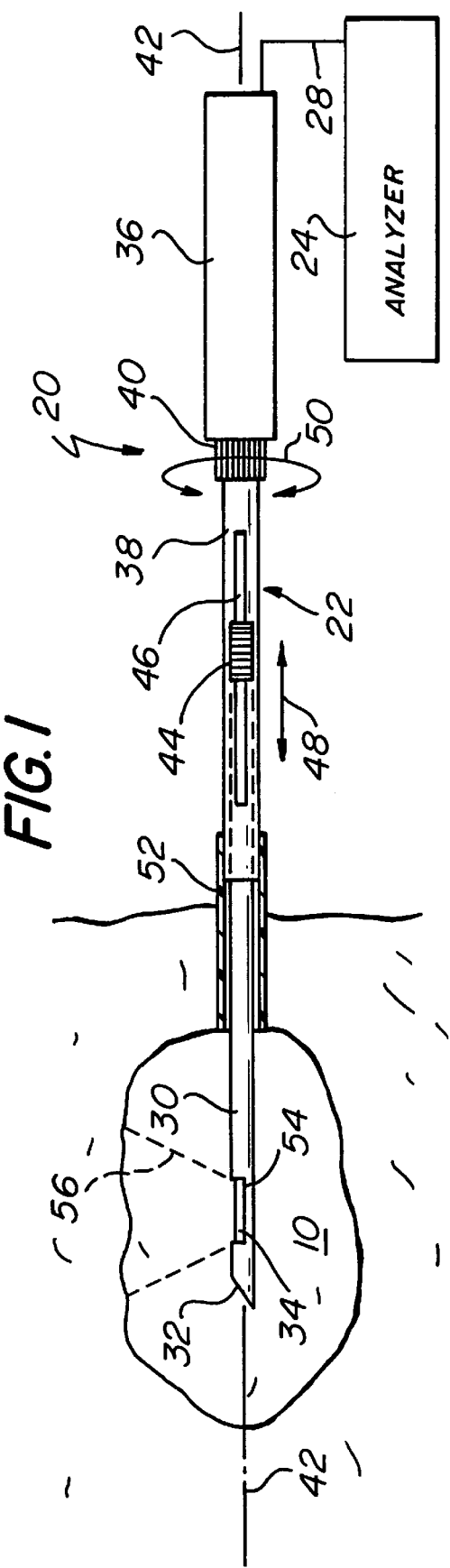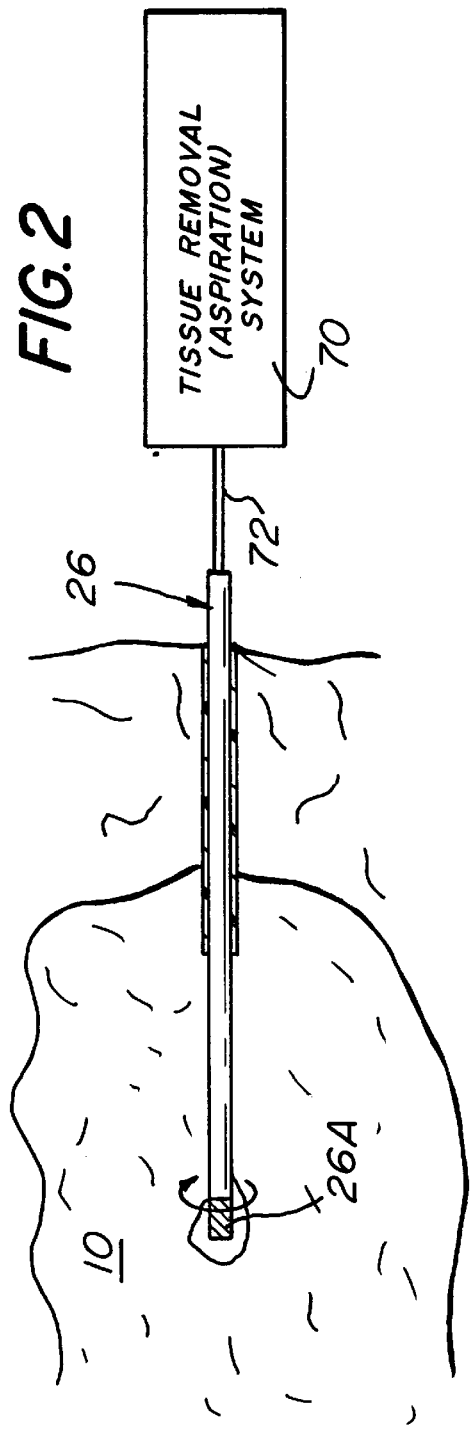

TUMOR LOCALIZATION AND REMOVAL SYSTEM USING PENETRATABLE DETECTION PROBE AND REMOVAL INSTRUMENT

BACKGROUND OF THE INVENTION

This invention relates generally to medical devices and methods of detection and treatment of cancer, and more particularly to minimally invasive medical systems including a radiation detecting probe for locating radioactively tagged tissue, e.g., a cancerous tumor or lymph node, within the body of the patient, and an instrument for removing or otherwise destroying that tissue.

The use of radioactive materials to tag tissue within a patient for effecting its localization and demarcation by radiation detecting devices has been disclosed in the medical literature for at least forty years. Significant developments in the localization and demarcation of tissue bearing radioactive isotope tags for diagnostic and/or therapeutic purposes have occurred since that time. In fact, it is now becoming an established modality in the diagnosis and/or treatment of certain diseases, e.g., cancer, to introduce monoclonal antibodies or other tumor or lymph node localizing agents tagged with a radioactive isotope (e.g., Technetium 99m, Indium 111, Iodine 123, and Iodine 125) into the body of the patient. Such radiopharmaceuticals tend to localize in particular tissue, such as the cancerous tissue, so that the gamma radiation emitted by the isotope agent can be detected by a radiation detector, e.g., a probe. In particular, the radiation detector or probe is disposed or positioned adjacent portion of the patient's body where the cancerous tissue is suspected to be in order to detect if any radiation is emanating from that site. If it is this indicates that cancerous tissue is likely to be found at that site.

Prior art, hand-held, radiation detecting probes particularly suitable for such cancer-finding applications are commercially available from the assignee of this invention, CareWise Medical Products, Inc. under the trademark C-TRAK, other probes are commercially available from Neoprobe Corporation under the trademark NEOPROBE 1000.

In U.S. Pat. Nos. 4,959,547 and 5,036,201 assigned to the same assignee as this invention there are disclosed hand-held radiation detecting probes having collimating means to establish the field of view or "solid angle of acceptance" of the probe. In U.S. Pat. Nos. 5,119,818 and 5,170,055, also assigned to the same assignee as this invention, there are disclosed hand-held radiation detecting probes and accessories optimized to biopsy radiolabeled tissues. In U.S. Pat. No. 4,801,803 (Denen et al.) there is also disclosed a hand-held radiation detecting probe.

In some medical applications it is desirable to conduct a biopsy or complete removal of or destruction the tissue identified by the radiation detecting probe as being the source of the radiation. i.e., the cancer site. For example, the institution of treatment with a toxic chemotherapeutic agent usually requires a biopsy of the identified site to assure that cancer cells are, in fact, present at that site. Similarly, Monoclonal Antibodies (MoAb) labeled with Technetium-99m or Indium-111 accumulate preferentially in specific cancers. Non-specific accumulation based on inflammation has been reported in the medical literature. Thus, a biopsy of MoAb and other tumor localization radiopharmaceutical identified sites is frequently necessary for patient management. Moreover the biopsying of radiopharmaceutical accumulation sites is essential to proving the specificity of any experimental MoAb or other tumor localizing or lymph node localizing radiopharmaceutical diagnostic or therapeutic drug.

While the prior art radiation detecting probes and/or biopsy probes, may be suitable for identifying the location of the radiation site, they leave something to be desired from the standpoint of facilitating the removal or other destruction of the detected cancerous tissue with minimum invasion of the patient.

OBJECTS OF THE INVENTION

Accordingly, it is a general object of this invention to provide a medical instrument system and method of use which overcomes the disadvantages of the prior art.

It is a further object of this invention to provide a medical instrument system including a radiation detecting probe arranged for use with a tissue removal/destroying instrument to facilitate the biopsy or removal of or destruction of tissue at a site identified by the probe as being a source of radiation produced by a radioactive pharmaceutical tagged to such tissue.

It is a further object of this invention to provide a minimal access, radiation detecting surgical probe.

It is a further object of this invention to provide a minimal access, radiation detecting surgical probe which is simple in construction and easy to use.

It is a further object of this invention to provide a radiation detecting surgical probe and associated analyzer which facilitates the location and demarcation of the bounds of radioactively tagged tissue, notwithstanding the presence of adjacent sources of radioactivity.

It is a further object of this invention to provide a radiation detecting surgical probe and associated collimator which facilitates the location of radioactively tagged tissue, notwithstanding the presence of adjacent sources of radioactivity.

It is still a further object of this invention to provide a system for detecting the location of radioactively tagged tissue, and for removing it via a minimally invasive instrument, which system enables the radioactivity of the removed tissue to be assayed for radioactivity to confirm that the desired tissue has been removed.

It is yet a further object of this invention to provide a minimal access, radiation detecting surgical probe which includes a removable portion which can be disposed of or resterilized and reused, and a non-removable portion to which a fresh or resterilized replacement portion can be connected, thereby enabling the non-removable portion of the surgical probe to be reused without requiring its resterilization.

SUMMARY OF THE INVENTION

These and other objects of the subject invention are achieved by providing a system and method of use for detecting and destroying living tumor tissue within the body of a living being. The system is arranged to be used with a tumor localizing radiopharmaceutical and basically comprises a tissue-penetratable radiation detector and an associated tumor removing or destroying instrument. To use the system a tumor localizing radiopharmaceutical is provided, e.g., injected, into the being's body so that it attaches itself to the living tumor tissue, whereupon it produces tumor-localizing radiation in the form of photons of different energies, e.g., characteristic x rays and full energy gamma rays, emanating from the living tumor tissue to which it has attached.

The radiation detecting means, e.g., a percutaneous needle probe having a scintillation crystal or a solid state semiconductor detector, is arranged to be inserted into the body of the being into the tagged tumor tissue. The radiation detecting means is movable to various positions with respect to the tumor, e.g., within it, for detecting the tumor localizing radiation from a plurality of directions and for providing a signal indicative of the three dimensional distribution of the living tumor tissue to which the radiopharmaceutical is attached.

The tumor removal/destroying instrument, e.g., a percutaneously introduced rotatable tip-resectoscope, is arranged to be inserted into the body of the being into the living tumor tissue via the same portal as used for the detecting probe, e.g., an introducer sheath, in order for the instrument to remove or otherwise destroy the living tumor tissue from within the tumor.

In accordance with one preferred aspect of this invention the instrument not only destroys the tagged tissue, but also removes it from the body of the being so that it can be assayed, e.g., tested for radiation continuously, to confirm that the removed tissue is radiolabeled cancerous tissue or radiolabeled lymph node tissue, and not irrelevant unlabeled healthy tissue.

In accordance with another aspect of this invention the system includes analyzing means coupled to the probe and which makes use of the known naturally occurring abundance of emitted photons of different energies produced by the particular radiopharmaceutical used, e.g., the ratio of characteristic x-ray photons to full energy gamma ray photons of that radiopharmaceutical, to provide the indication of the three dimensional distribution of the living tumor tissue to which the radiopharmaceutical is attached.

In accordance with yet another aspect of the invention the radiation detecting means is provided with a collimator larger in diameter, e.g., at least 1 mm larger, than the outside diameter of the detector. The collimator serves as a radiation detection enhancing means. In this regard it blocks radiation to the radiation detector, e.g., the scintillation crystal or solid state semiconductor, from various directions. In addition it increases the number of ionizing rays incident on the detector from rays accepted into the field of view of the collimator.

DESCRIPTION OF THE DRAWING

Other objects and many attendant features of this invention will become readily appreciated as the same becomes better understood by reference to the following detailed description when considered in connection with the accompanying drawing wherein:

FIG. 1 is an illustration of portions of the system of this invention for detecting the presence of a radioactively tagged tumor within the body of a living being and for effecting the removal of that tissue percutaneously, with the portions of the system shown in this figure being those portion which detect the radioactively tagged tissue;

FIG. 2 is an illustration like that of FIG. 1 showing other portions of the system of FIG. 1, namely, those portions of the system for removing the radioactively tagged tissue;

DETAILED DESCRIPTION OF THE PREFERRED EMBODIMENTS

Figure 3:
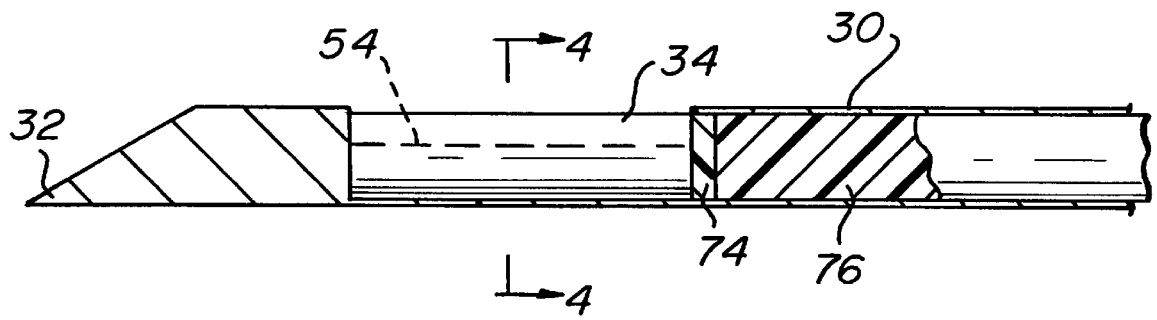
FIG. 3 is an enlarged view, partially in section, of the distal end of the radiation detecting probe forming a portion of the system shown in FIG. 1.

Referring now to the drawing where like reference numerals refer to like parts there is shown at 20 in FIGS. 1 and 2, a system constructed in accordance with this invention. The system 20 is arranged to be used with any suitable radiopharmaceutical which is injected or otherwise introduced into the body of the being to be treated for specific uptake by the suspected cancer tissue or sentinel lymph node so that the system can determine the location of that cancer or lymph node and remove it with minimal invasion to the patient's body. To that end the system 20 basically comprises a minimal access surgical probe 22 and an associated analyzer 24 for detecting radiation emanating from the hidden source in a patient, e.g., a tumor 10 tagged with the radiopharmaceutical, to localize that tissue, and a minimal access instrument 26 for removing or otherwise destroying the tagged tissue.

The details of various embodiments of the probe 22 of this invention will be described in detail later. Suffice it to state that in each case the probe is constructed to detect radiation impinging its sensor component and to provide an electrical signal indicative of the photons of radiation received. This electrical signal is provided from the probe via a cable 28 to the analyzer 24. The analyzer is preferable constructed in accordance with the teachings of our copending U.S. patent application Ser. No. 08/430,589, filed on Apr. 28, 1995, entitled Apparatus And Methods For Determining Spatial Coordinates Of Radiolabelled Tissue Using Gamma-rays And Associated Characteristic X-rays now U.S. Pat. No. 5,694,933, which is assigned to the same assignee as this invention and whose disclosure is incorporated by reference herein.

The details and operation of the analyzer 24 will not be reiterated herein in the interest of brevity. Suffice it to state that the analyzer 24 provides output signals via a graphic display and associated audible annunciator which are indicative of the radiation detected by the probe, after removal of any extraneous signals (e.g., Compton scattered radiation). The output signals of the analyzer 24 enable the user of the system 20 to accurately determine the presence of near field radiation activity, e.g., a radioactively tagged tumor, notwithstanding the existence of any far field sources (e.g., another tumor or a site of non-specific uptake, such as the liver or blood pool) which could be contributing to the radiation detected. Thus, like the system disclosed in our aforementioned copending application, the system 20 of this invention makes use of a probe 22 to find the radioactively tagged tissue, e.g., tumor or lymph node.

The probe 22 of this invention accomplishes its task by minimal invasive percutaneous penetration into the patient's body at the suspected situs of the tumor, while the analyzer monitors the radiation picked up by the probe. By monitoring the radiation detected from the radiopharmaceutically tagged tissue (e.g., gamma radiation, X radiation and/or annihilation radiation) the analyzer provides signals to the user to guide him/her so that the probe can be inserted within the tumor (as will be described in detail later). Plural radiation readings can then be made at various positions within the tumor to determine its boundaries, i.e., its three dimensional distribution. Then the probe 22 can be removed, leaving a portal, e.g., an introducer sheath (to be described later), in place extending into the vicinity of the tumor. The tissue removal/destroying instrument 26 can then be inserted through the portal to remove or sample the tumor or lymph node and/or ablate or otherwise destroy the tumor or lymph node tissue.

In accordance with a preferred aspect of this invention the sampled and/or ablated tumor tissue is removed from the patient's a body by a portion of the system (to be described later) to survey it for radioactivity in order to determine if the tissue removed is, in fact, tumor tissue and not healthy tissue. The probe can be reinserted into the portal (or another portal) and oriented, as desired, to determine if any residual tumor remains. If so, the process can repeated until no further radioactively tagged tissue, e.g., tumor, remains.

Figure 5:
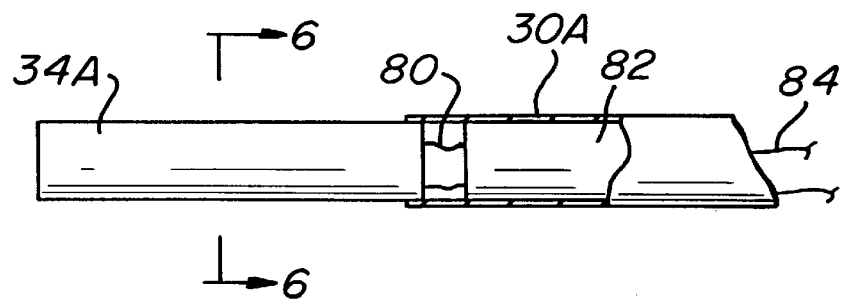
FIG. 5 is an enlarged view, partially in section, of the distal end of an alternative embodiment of a radiation detecting probe forming a portion of the system of FIG. 1.

As best seen in FIG. 1 the probe 22 is an elongated device having a small diameter linear distal end portion. This portion is in the form of a hollow needle 30 having a sharp tip 32. The needle is of a small outside diameter, e.g., 2–7 mm, and has a very thin wall thickness, e.g., 0.01–0.02 inch (0.25–0.5 mm). Preferably the needle is formed of a rigid, biocompatible material. That material may be stainless steel, molybdenum, tungsten, tin or other metals, or even non-metals, depending upon whether or not the material of the needle is to serve as a barrier to radiation reaching its detector element. The radiation detector element or sensor is denoted by the reference number 34 and will be described in detail later. Suffice it for now to state that the radiation sensor may comprise a scintillation crystal or may comprise a solid state semiconductor. In the embodiment of the probe of FIG. 1 the sensor 34 is located within the hollow interior of the needle 30 adjacent its tip 32. Alternatively, the sensor may be located so that at least a portion of it extends beyond or distally of the probe's tip, as shown in FIG. 5. In such a case the tip of the probe need not be sharp.

The proximal end of the probe 22 is in the form of a cylindrically shaped handle 36 which is arranged to be grasped by the user of the system 20 so that he/she can manipulate and use the probe 22. If the radiation detector of the probe utilizes a scintillation crystal sensor (to be described later) the handle 36 may contain a device to convert light to an electrical signal, e.g., a conventional photomultiplier tube, and an associated light transmission member to carry the bursts or flashes of light produced by the crystal in response to impinging radiation to the photomultiplier tube. Alternatively the photomultiplier tube may be located outside the probe, e.g.; in the analyzer 26 or in some member connected between the probe and the analyzer. If the radiation detector is a solid state semiconductor component, then the handle 36 may contain the amplifier electronics for that component. Alternatively, the electronics may be located outside the probe, e.g., in the analyzer 26 or in some member located between the probe and the analyzer. In fact, it is also contemplated that by use of microminiaturization of electronics the analyzer circuitry can be resident in the probe's handle.

As shown in FIG. 1 probe 22 includes a sleeve or tube 38 which is rotatably mounted, via a coupling 40, on the front end of the handle 36. The sleeve 38 is arranged to be rotated to any angular position about its central longitudinal axis 42, but such action is not mandatory. Thus, the sleeve 38 need not be rotatable with respect to the handle. As such the rotatable coupling 42 is unnecessary.

The sleeve 38 is a thin walled member, e.g., of the same wall thickness as the needle 30 and has an inside diameter is just slightly larger than the outside diameter of the needle 30. The needle containing the detector 34 is mounted within the interior of the sleeve 38 in the probe 22 of FIG. 1 so that it can be slid longitudinally with respect thereto along the axis 42 by operation of a slide button 44 coupled to it. The slide button 44 extends through an elongated slot 46 in the wall of the sleeve 38. Thus, by sliding the button 44 distally the needle 30 can be slid in the distal direction, and by sliding the button 44 proximally the needle 30 can be slid in the proximal direction, as represented by the double-headed arrow 48 in FIG. 1. Moreover, rotation of the sleeve 38 of the probe of FIG. 1 about its axis 42 to any angular orientation by rotation of the coupling 40 effects the concomitant rotation of the needle to that angular orientation. The sleeve is arranged to be rotated by rotation of the coupling 40 a full 360 degrees in either direction about the axis 42 as represented by the double-headed arrow 50.

The sleeve 38 and the needle 30 contained within it are preferably releasably connected to the handle by a releasable coupling (not shown) to enable them to be removed from the handle 36, e.g., for sterilization and reuse or disposal. Thus, a fresh or resterilized sleeve 38 and associated needle 30 may be mounted on the probe handle 36 whenever such action is desired.

The previously mentioned introducer sheath is shown in FIG. 1 and is designated by the reference number 52. As can be seen therein the sheath 52 is in the form of a small diameter tube. The sheath is releasably mounted, e.g., frictionally held, on the sleeve 38 of the probe 22 so that it can be carried by the probe into the body of the patient when the probe's needle 30 is inserted percutaneously into the patient. The sheath 52 is of any suitable construction and material to form a portal which can be left in place, when desired. In particular, the sheath 52 enables the probe 22 to be removed from it once the tumor 10 has been located and the probe's tip disposed within it. Then the instrument 26 can be inserted through the sheath to effect the destruction and/or removal of the tumor tissue. To facilitate its placement the sheath 52 has a sharpened distal end (not shown).

The sensor 34 has a predetermined solid angle of acceptance of radiation or field of view depending upon its shape and construction and whether or not any portion of it is covered by a radiation blocking material, e.g., a collimator. That field of view may be spherical, hemispherical with a "front looking" orientation (i.e., looking outward along the longitudinal axis of the device) or a "side looking" orientation (i.e., looking outward perpendicular to the longitudinal axis of the device), or some other shape, such as a quadrant or other wedge shaped sector oriented in the desired direction.

Figure 4:
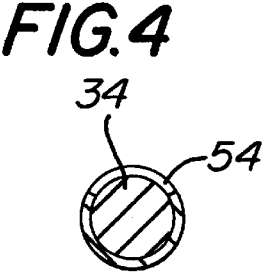
FIG. 4 is a sectional view taken along line 4—4 of FIG. 3.
Figure 6:
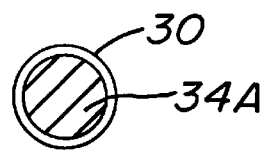
FIG. 6 is a sectional view taken along line 6—6 of FIG. 5.

In the embodiment shown in FIG. 1 the needle 30 includes a rectangular opening or window 54 whose length extends the length of the sensor 34 and whose width extends about approximately 120 degrees of the circumference of the needle wall, as shown in FIGS. 1, 3, and 4. The window 54 serves as a collimator to reduce the field of view of the sensor 34 to a wedge shaped sector 56, like that shown in FIG. 1. To achieve that end the needle is formed of a radiation blocking or radiation resistant material, e.g., is selected to have a higher atomic number than stainless steel. Thus, the needle wall forms a barrier to radiation passing through it to the sensor 34. Metals such as molybdenum, tungsten, tin, etc., may be used for this purpose. Alternatively the needle may be formed of stainless steel but having a barrier wall 60 of a radiation resistant material mounted on it to form a collimator. That barrier wall may be in the form of an elongated rod like member having a generally U-shaped longitudinal recess in it for longitudinal receipt of the portion of the needle 30 contiguous with the sensor 34. The open side of the U-shaped recess establishes the boundaries of the field of view of the sensor.

It should be noted that it is also contemplated that the orientation of the field of view of the probe, e.g., front looking or side looking, may be selectively reversible or switchable. Such switchability may be accomplished by mounting a sensor 34 in a needle 30 having an axially facing open end or window, a contiguous side or laterally facing open slot or window, and a high atomic number flowable radiation blocking material located in one of the windows for movement into the other of the windows and vice versa. Two examples of such flowable radiation blocking materials are mercury and a tungsten powder slurry. When the flowable material is located within the front window the probe will be side looking. Moving the flowable material out of the front window and into the side window converts the probe to a front looking device.

As should be appreciated by those skilled in the art, when the probe 22 is in position within the body of the patient the needle can be extended either distally or retracted proximally to bring the sensor to any desired position along the longitudinal axis 42. Thus, any radiation within the sensor's field of view, i.e., the sector extending laterally of the longitudinal axis 42, will be received by the sensor. By rotating the sleeve 38 and the needle 30 coupled to it at any longitudinal position along the axis 42 the sensor can sequentially examine the tissue surrounding the axis of the probe for radioactivity. Thus, one can directionally look at any sector, at any position along the longitudinal axis of the probe and can rotate the probe to get a circumferential assessment of radiation at that longitudinal position. This ability enables the system to find the tumor and map its distribution from within it.

For example, in order to determine the general center of the tumor one can extend the probe into the patient's body at the suspected tumor site while monitoring the analyzer for the presence of some robust radiation. When radiation is detected the outer margin of the tumor along the axis 42 will be known since the field of view of the probe is lateral. If desired, once radiation is detected the needle can be rotated to determine the degree of symmetry of detected radiation surrounding that longitudinal position on the axis 42. The probe's needle can then be inserted deeper along axis, while monitoring the radiation. This procedure can be repeated as necessary, e.g., every centimeter, to determine the furthest boundary of the tumor along axis 42. Since the amount of radiation received by the probe is proportional to the mass of the radioactively tagged tumor tissue and its distribution in space a circumferential assay, i.e., taking radiation readings at various rotational orientations about axis 42, will provide a good indication regarding the margins of the tumor. For example, if radiation is detected from all directions about the axis 42, and the detected radiation is generally symmetrical, then it is known that the probe's axis is generally centered in the tumor. Thus, by conducting a circumferential radiation assessment at each position along axis 42 the general center and general boundaries of the tumor can be determined.

Once the position of the tumor determined it can be treated using any conventional or non-conventional technique. For example, externally applied radiation can be brought to bear on the tumor to kill it, such as disclosed and claimed in copending U.S. patent application Ser. No. 08/509,627, filed on Jul. 31, 1995, entitled Apparatus And Methods For Providing Attenuation Guidance And Tumor Targeting For External Beam Radiation Therapy Administration, which is assigned to the same assignee as this invention and whose disclosure is also incorporated by reference herein.

Alternatively, and in accordance with a preferred aspect of the invention, once the tumor has been located, the probe 22 is removed from the patient's body and the instrument 26 inserted to remove or otherwise destroy the cancerous tissue.

It should be noted that the subject invention can make use of any type of instrument for removing and/or otherwise destroying the cancerous, e.g., radioactively tagged, tissue once the probe 22 determines the location of that tissue. In the embodiment shown herein the instrument 26 comprises an elongated rotatable-tip "resectoscope" of small diameter, suitable for extension through the sheath 52 to the situs of the tumor. The resectoscope includes a rotatable cutting tip 26A at its distal end to remove, e.g., cut away small pieces or chips, of the radioactively tagged tumor.

In accordance with one preferred aspect of this invention the removed tissue pieces or chips are tested for radioactivity as they are removed to ensure that the procedure is, in fact, removing tumor, not healthy tissue. Thus, the system 20 includes a tissue removal or aspiration system 70 which is coupled to a lumen 72 into which tissue pieces or chips are drawn during the operation of the resectoscope. A radiation detector (not shown) forms a portion of the system 20 and is coupled to the aspiration system to monitor the chips as they are removed to determine if they are radioactive.

It should be noted at this juncture that even if there are other sources of radiation, e.g., sources of non-specific uptake, in the general vicinity of the tumor that should not present a significant problem to detecting and removing tumor using the subject invention. In this regard the probe is used as described above to determine the general location of the tumor. Then the probe is removed and replaced by the tumor removing instrument. That instrument is then utilized to begin to remove the radioactively tagged tissue, while the operator continuously assesses the removed tissue chips for radioactivity to confirm tumor removal. If a portion of the tumor escapes detection and removal from the initial site of probe penetration, then the probe can be reinserted into a different site from which radiation is emanating and the probe operated in a similar manner to provide an indication of the general vicinity and boundaries of the remaining tumor. Then the probe can be removed and the tissue removal instrument introduced into the new site to remove the radioactively tagged tissue thereat, while assessing the radioactivity of the removed tissue chips. If the chips removed are not radioactive, that indicates that the removal instrument is outside the margins of the tumor. The tumor location/removal process can be repeated from as many directions/positions and as many times as necessary until no further near-field radiation is detected by the probe and the removed chips are not radioactive, thereby indicating complete removal of the tumor or the lymph node. An optical or other imaging system (not shown) can be inserted through the introducer sheath 52 after the tissue removal instrument 26 has completed its operation to provide the practitioner with a visual image of the situs of the removed tissue. Moreover, the tumor removal process can be monitored by real time ultrasound to prevent damage to adjacent large blood vessels.

In the interest of minimum patient invasion, it is preferred that the needle probe be of a sufficiently small size, e.g., 2–7 mm in diameter, for easy percutaneous introduction into the suspected tumor site. The tissue removal/destroying instrument should also be of a similar diameter.

While the system 20 may be used without an analyzer 26 constructed in accordance with the teachings of our aforementioned copending patent application Ser. No. 08/430,589, it is preferable to use such an analyzer. In this regard the analyzer 26 can measure the characteristic x-ray photons and full energy gamma ray photons received by the probe's sensor to determine if the ratio of the characteristic x-ray photons to the full energy gamma ray photons is appropriate for the particular radiopharmaceutical used to tag the tissue, i.e., corresponds to the natural abundance of the characteristic x-rays and full energy gamma rays for that radiopharmaceutical. If the ratio is appropriate that fact enables the operator to accurately determine the near field location of the radioactively tagged tumor since there could not be any far field source of radiation which could interfere with the precise location of the tumor (a source of far field radiation would result in an improper ratio of characteristic x-rays to full energy gamma rays). Conversely, an inappropriate ratio, e.g., a reading of significantly more full energy gamma-ray photons than characteristic x-ray photons, will indicate that the source of radiation is far field. Thus, the probe should be moved to a new position, e.g., a new puncture made, until an appropriate ratio of characteristic x-ray photons to full energy gamma ray photons is detected.

The subject invention has wide applicability for treatment of various types of cancers. For example, in the treatment of breast cancer once a suspected tumor has been located, e.g., palpated, a radioactive tracer, e.g., 1000 microcuries of Technetium-Sulfur-Colloid, can be injected in a confined volume, e.g., 1–8 cc, around the margins of the tumor. If the primary tumor is non-palpable it can be labelled under ultrasound guidance. In any case, a short period of time, e.g., a ½ hour, after the radioactive tracer has been injected at the tumor site some portion, e.g., less than 1% to more than 50%, of the colloid will have migrated to those lymph nodes which drain the tumor. The subject invention can be used to remove the tumor in the same manner as described above. Then a fresh or sterilized instrument used to locate and remove whichever draining lymph nodes exhibit radioactivity. The detection and removal of the draining lymph node(s) is effected in the same manner as the removal of the primary tumor.

As should be appreciated by those skilled in the art, the "sentinel node" procedure, which is the accepted modality of treatment for melanoma, and which will likely be the accepted modality of treatment for breast cancer can be effected percutaneously using the subject invention, instead of through conventional cut-down or open surgery, e.g., lumpectomy, as is the case at present. Moreover, the subject invention has particular utility for prostate cancer treatment, wherein the primary tumor and any draining lymph nodes exhibiting radioactivity (lymph nodes having radioactively tagged cancer cells) can be removed with minimum invasion to the patient so that no source of cancer remains.

Referring now to FIGS. 3–6 the details of various exemplary embodiments of radiation detecting probes 22 will now be described. Each probe uses a radiation sensing element or sensor which can be of any suitable type. In the probe 22 the radiation sensor 34 comprises a Cesium-Iodide-Thallium, mirror polished scintillator crystal, located within a hollow cavity in the needle 30. Other scintillator crystals, e.g., Lutecium Orthosilicate, Gallium Orthosilicate, etc., can be used as well. An optical conductor 74, such as a thin layer of silicone optical grease, gel or liquid, is preferably provided contiguous with the proximal surface of the scintillator crystal 34 for conveying the flashes of light from the scintillator (when radiation is received by it) to a section of an optical light pipe 76 located within the probe. The proximal end of the optical light pipe terminates in an optical connector or coupling (not shown) in the probe. That coupling is releasably secured to a mating optical coupling (not shown) within the handle 36 of the probe. The mating coupling is in turn connected to the photomultiplier tube located within the handle. The electrical signals produced by the photomultiplier tube in response to light flashes or bursts produced by the scintillation crystal sensor 34 are provided, via the cable 28, to the analyzer 26. Alternatively, the photomultiplier tube may be located within the analyzer 26 and an optic fiber conductor used to convey the flashes of light from the scintillator to the analyzer-mounted photomultiplier tube. In either case, the flashes of light produced by the scintillator 34 in response to radiation photons impinging it are converted into electrical signals and are processed by the analyzer 26 to represent the radiation received by the probe. The needle 34 and its associated radiation detector, light pipe and optic fiber coupling are preferably assembled to form a releasably securable, replaceable unit. By so doing, the replaceable needle unit can be removed from the remaining portion, e.g., the handle, of the probe 22 by disconnecting the couplings. The handle unit can then be reused with a fresh or resterilized needle unit. The removed needle unit can be discarded or resterilized for subsequent reuse.

As an alternative to a scintillation crystal needle probe of FIG. 3, the subject invention can make use of a solid state semiconductor radiation detector 34A, e.g., a Cadmium-Zinc-Telluride element. That element may be mounted at the distal end of a blunt-ended needle 30A, like shown in FIG. 5 or can be located within a sharp-ended needle under a collimating window (not shown), depending on the desired application. In the embodiment of FIG. 3 the field of view of the detector 34A is spherical. The detector element 34A, being a solid state device, includes a pair of leads or wires 80 which are connected to a preamplifier 82, e.g., a field effect transistor located within the handle 36. The needle 30A and its associated detector 34 are preferably formed as an integral, replaceable unit so that they can be removed from the handle 36. Thus, the handle 36 can be used with a fresh or resterilized needle unit, and the removed needle unit can be disposed or resterilization for reuse as discussed above.

The output of the FET is provided via wires 84 in the probe handle 36 to the cable 28 serving as the input to the analyzer 26. As should be appreciated by those skilled in the art, with this type of probe the system need not include a photomultiplier tube to convert light flashes to electrical signals since the output of the semiconductor detector is already an electrical signal indicative of received radiation. A Peltier effect cooler (not shown) may be used in conjunction the Cadmium-Zinc-Telluride solid state detector 34A to enhance spectral resolution.

The disposable/replaceable needle unit of either the scintillation crystal type or the solid state semiconductor type as discussed above is preferably initially stored in a sterile bag or package (not shown). The package or bag preferably has a readily openable mouth, e.g., a "zip-lock" or "pull-tab", to provide ready access to the needle unit. Thus, the needle unit can be removed from the package under sterile conditions, e.g., in an operating room, and then be mounted on the handle 36 of the probe 22 for use. An extendable, e.g., collapsibly folded, sterile flexible barrier sheath (not shown)

may be connected to the proximal end of the needle unit for extension, e.g., unfolding, over a part of the system 20, e.g., the probe's handle 36 and the cable 28. This feature enables the user to isolate the probe 22 and associated cable 26 from contamination during use of the system 20 and assures a sterile operating environment. In the further interests of preventing contamination of the system 20 an isolating shroud or cover (not shown) may be provided over the analyzer.

It must be pointed out at this juncture that the radiation detecting probes of this invention can be constructed in various ways to provide either a full spherical field of view, i.e., to detect radiation from all directions, or a restricted field of view. Moreover, the field of view may be lateral or side looking (i.e., extend around an axis perpendicular to the longitudinal axis of the probe) or may be axial or front looking (i.e., extend from the distal end of the probe around the longitudinal axis) depending upon the construction of the probe and the location of its radiation detecting element. A spherical detector probe, like that of FIG. 5, may be desirable to provide initial tumor localization, since it will detect radiation from all directions. Thus, it will provide a maximum signal when it is located within the central area of the tumor. If preferential detection, i.e., detection of radiation within a confined field of view, either lateral or axial, is desired the spherical radiation detecting probe can still be used, provided it is used in combination with a radiation blocking member, to provide the specific or confined field of view, e.g., a quadrant. For example, the radiation blocking member may be a sleeve or sheath (not shown) formed of a radiation resistant material and which has a radiation transmissive window or opening therein. The probe is inserted in the sheath so that its spherical detector is at the window, whereupon the field of view of the detector will be limited to that established by the sheath's window.

Figure 8:
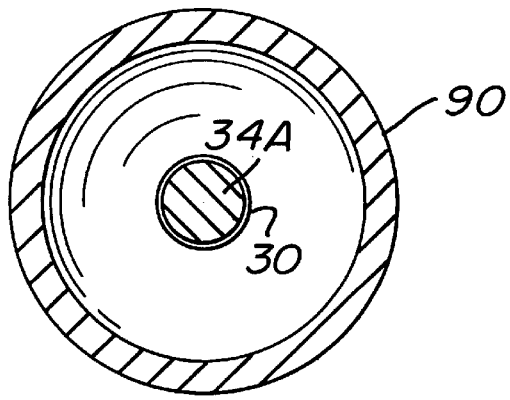
FIG. 8 is a sectional view taken along line 8—8 of FIG. 7.

In order to increase the radiation detecting sensitivity of a probe of this invention, while providing it with a confined or narrow solid angle of acceptance (field of view) the probe is preferably provided with a detection-enhancing collimator for disposition adjacent its radiation detecting element. For example, as shown in FIG. 8 an ovate shaped collimator member 90 formed of a radiation resistant or blocking material, e.g., tungsten, and having an open end is mounted on the distal end of the probe 22. The inside diameter of the collimator's open end is significantly larger than the outside diameter of the radiation sensor (e.g., 1 cm compared to 5 mm) and is disposed symmetrically thereabout and with the open end of the collimator being located adjacent the radiation detecting element or sensor 34A. The collimator is constructed of a radiation blocking material so that it effectively blocks any radiation from passing through it to the detector element 34A. Thus, the solid angle of acceptance for the detector will be that established by the open end of the collimator. Since the inside diameter of the open end of collimator is significantly larger, e.g., 1 cm, than the diameter, e.g., 5 mm, of the probe radiation rays which would have otherwise been outside the field of view of the probe may never the less enter into the window or open end of the collimator to bounce off of its inner surface to impinge the detector 34A. In addition rays which enter into the collimator through its open end will cause the collimator material to produce x-ray fluorescence which the detector element will also pick up, thereby increasing the sensitivity of the detector. The collimator can be any size and shape, e.g., at least 1 mm larger in diameter than the outside diameter of the radiation detector component so that the collimator enhances the operation of the radiation detector by both blocking unwanted radiation to the detector and increasing the number of ionizing rays incident on the detector from rays accepted into the solid angle or field of view of the collimator. In this connection the both incident rays bouncing off the collimator inner surface ("Compton scattered rays") and x-ray fluorescence rays from the excited inner surface of the collimator are added to those rays directly incident upon the detector. For example, a 3 mm internal diameter collimator surrounding a 2 mm external diameter detector approximately doubles the counts measured at contact with the point source of radiation. If the collimator is constructed to be able to be readily removed, e.g., snapped apart, one can use the radiation detecting probe with the collimator in position to localize the radioactively tagged tissue from the skin surface and then remove the collimator to enable unimpeded tissue penetration by the full length of the probe's needle.

Figure 7:
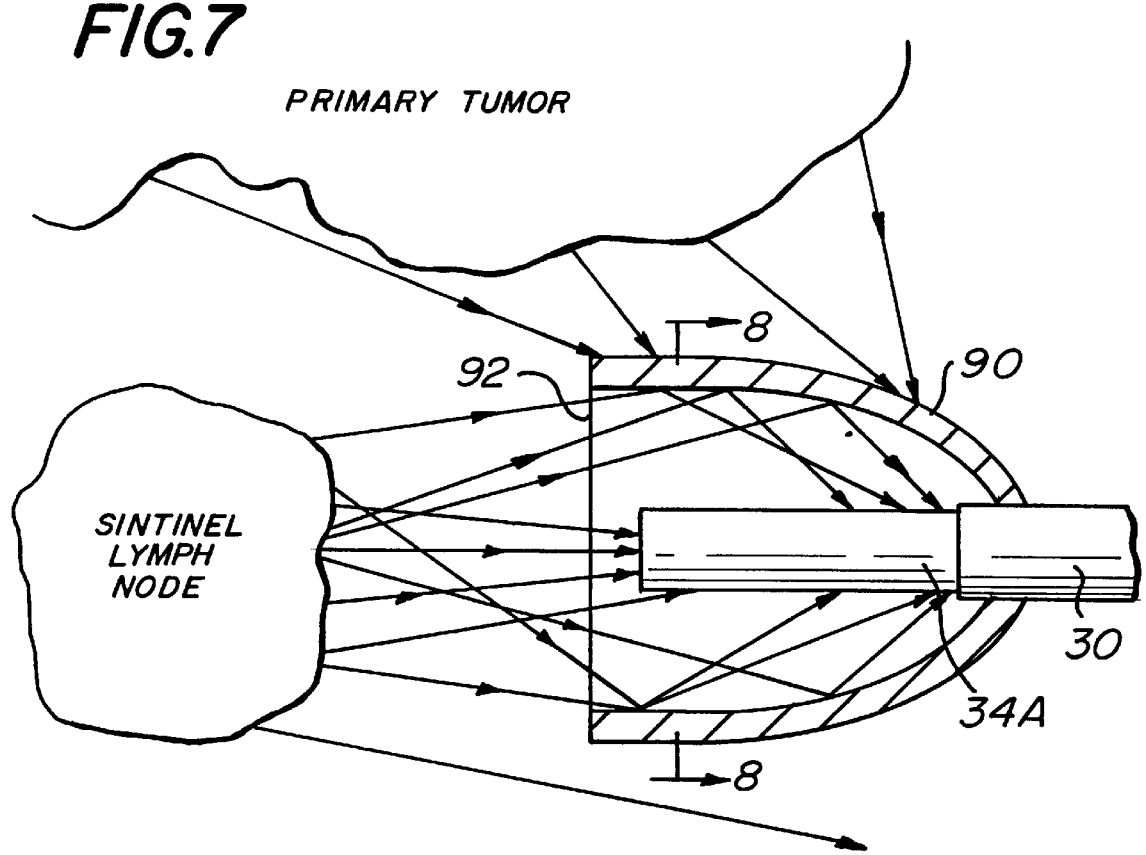
FIG. 7 is an illustration of an the distal end of an alternative embodiment of a radiation detecting probe forming a portion of the system of FIG. 1 shown during its usage to detect a cancerous or non-cancerous sentinel lymph node adjacent a cancerous primary tumor (e.g., breast tumor)

The use of a collimator to increase sensitivity while providing a narrow solid angle of acceptance should be of considerable utility for various cancer treatment applications. For example, if it is desired to locate the first draining lymph node (the sentinel node) from a primary breast tumor before removal of the primary tumor, such as shown in FIG. 7, a small diameter, e.g., 5 mm, probe like that described heretofore may not be adequate for the task. This is particularly true if the system does not make use of an analyzer constructed in accordance with the teachings of our aforementioned patent application to exclude the effects of far field sources of intense radiation. Thus, for such sentinel node applications the collimator can be used to increase the sensitivity of the probe to the small amount of radiation emanating from the draining lymph node, while shielding out the intense radiation emanating from the adjacent primary tumor.

Other collimators than that described above can be used in the system 20 of this invention. For example, a collimator suitable for use with this invention may comprise a disk-like member having a central opening therein and mounting means for mounting it onto the needle probe. In particular, the disk-like collimator member when mounted will overlie and cover the distal end portion of the probe, whereupon the disk-like cover member blocks radiation from passing therethrough to establish a desired field of view. The system 20 may make use of interchangeable sets of collimators. Each interchangeable set of collimators may be designed to have a different focal point in the depth axis and/or accommodation of different size lesions. Choice of the collimator would be based on the individual's Nuclear Medicine information and anatomical differences.

In accordance with other aspect of this invention a disposable shield (not shown) is preferably provided for the probe to protect it from contamination. The shield comprises a tubular member having a distal end from which a disk-like cover member projects outward radially. The tubular member is arranged to be located within a passageway in the distal end of the probe, with the disk-like cover member overlying and covering the distal end portion of the probe.

While the tissue removal/destroying instrument 26 shown in FIG. 2 has been described as being a rotatable tip resectoscope, such a device is merely exemplary. Thus, the instrument 26 used to remove the radioactive tagged tissue can be any small diameter instrument for cutting, chipping, or otherwise ablating the tagged tissue. It is preferred that the operation of the instrument provide tissue pieces or fragments which are suitable for examination for radioactivity to confirm that the tissue being removed is cancerous and not healthy tissue. Thus, side cutting or end cutting biopsy devices may be used.

It is contemplated that other means can be used to effect the destruction and/or removal of the detected tumor without making use of a cutter to remove the tumor tissue. In this regard the tissue destroying instrument 26 can make use of cancer cell necrotizing agents, such as, high-intensity ultrasound, microwave energy, laser energy, heat, electricity (e.g., electro-cutting, electro-coagulation diathermy), or chemical introduction to destroy the tagged tissue. With respect to the latter, the instrument may be arranged to provide injections of minimally invasive tissue destructive agents. Those agent may include tumor destructive compounds, such as free radical promoters, copper ions, iron ions, oxidants, iodine, and tissue digestive enzymes, as well as hyperosmotic and hypoosmotic materials, absolute alcohol, and other chemical tissue destroying agents. Moreover, the instrument may be arranged to provide radioactive seed implants as the necrotizing agent. Further still the necrotizing agent may be provided either internally to the tagged tissue, e.g., through percutaneous or cut down introduction, or externally from some external device or machine.

Without further elaboration the foregoing will so fully illustrate our invention that others may, by applying current or future knowledge, adopt the same for use under various conditions of service.

What is claimed is:

1. A system for determining the three dimensional representation of living tumor tissue within the body of a living being, said system comprising a tumor localizing radiopharmaceutical and small diameter penetratable radiation detecting means, said tumor localizing radiopharmaceutical being attached to the living tumor tissue, whereupon said radiopharmaceutical produces tumor-localizing radiation from the living tumor tissue, said tumor-localizing radiation comprising photons of different energies produced by said radiopharmaceutical, said small diameter penetratable radiation detecting means being arranged to be inserted into the body of the being with minimal invasion of the being via a percutaneous incision or access port and being movable along a path within the tumor tissue for location at various positions within the tumor tissue for detecting said tumor localizing radiation from a plurality of directions therein to provide an indication of the three dimensional distribution of the living tumor tissue to which said radiopharmaceutical is attached and for providing a signal indicative thereof.

2. The system of claim 1 wherein said penetratable radiation detecting means is an elongated member having a longitudinal axis arranged to be located along said path and to be rotated about said longitudinal axis to various angular positions.

3. The system of claim 1 wherein said penetratable radiation detecting means is an elongated member having a longitudinal axis and arranged to penetrate the tumor tissue and be moved within the tumor tissue to various positions along said path.

4. The system of claim 3 wherein said penetratable radiation detecting means is arranged to be rotated about said longitudinal axis to various angular positions.

5. The system of claim 1 additionally comprising tissue destroying means for destroying the living tumor tissue.

6. The system of claim 5 wherein said tissue destroying means is arranged for providing a dose of a necrotizing agent therefrom.

7. The system of claim 6 wherein said necrotizing agent comprises a radioactive agent.

8. The system of claim 7 wherein said radioactive agent is in a locally persistent form arranged for location adjacent the situs of the living tumor tissue, whereupon said radioactive agent produces radiation emissions therefrom to necrotize the living tumor tissue.

9. The system of claim 7 wherein said radioactive agent produces emissions of one or more selected from the group consisting of alpha rays, beta rays, gamma rays, x rays, and neutrons, and wherein said necrotizing means provides said emissions to the living tumor tissue.

10. The system of claim 6 wherein said necrotizing agent comprises a pharmacologic substance.

11. The system of claim 6 wherein said necrotizing agent comprises ultrasonic waves, and wherein said necrotizing means provides said ultrasonic waves to the living tumor tissue.

12. The system of claim 6 wherein said necrotizing agent comprises a laser beam, and wherein said necrotizing means provides said laser beam to the living tumor tissue.

13. The system of claim 6 wherein said necrotizing agent is thermal, and wherein said necrotizing means provides said thermal agent to the living tumor tissue.

14. The system of claim 13 wherein said thermal agent necrotizes the living tumor tissue by the heating it.

15. The system of claim 13 wherein said thermal agent necrotizes the living tumor tissue by cooling it.

16. The system of claim 1 additionally comprising means for removing at least a portion of the living tumor tissue from the body of the living being.

17. The system of claim 16 wherein said means for removing operates on a continuing basis.

18. The system of claim 16 additionally comprising means for determining if said removed portion of the living tumor tissue is radioactive.

19. The system of claim 1 wherein said penetratable radiation detecting means is arranged for detecting said tumor localizing radiation from a plurality of directions therein utilizing the known naturally occurring abundance of emitted photons of different energies of said radiopharmaceutical as a reference factor.

20. The system of claim 19 additionally comprising tissue destroying means for destroying the living tumor tissue, said tissue destroying means being arranged for percutaneous introduction into the body of the being.

21. The system of claim 1 wherein said penetratable radiation detecting means is an elongated device having a longitudinal axis, and a sensor having a predetermined field of view for detecting radiation with said field of view.

22. The system of claim 21 wherein said field of view extends laterally of said longitudinal axis.

23. The system of claim 21 additionally comprising collimator means for limiting said field of view.

24. The system of claim 21 wherein said penetratable radiation detecting means comprises a needle.

25. The system of claim 21 additionally comprising radiation detection enhancing means comprising a barrier wall disposed adjacent said sensor for blocking radiation to said sensor from various directions, said barrier wall having an opening through which radiation may pass for reflection from said barrier wall to said sensor.

26. The system of claim 25 wherein said barrier wall is ovate in shape and wherein said opening is at one end thereof.

27. The system of claim 25 wherein said barrier wall is formed of a material which fluoresces to produce x-rays when exposed to radiation from said living tumor tissue, and wherein said barrier wall is disposed so that said sensor receives the x-rays produced by the fluorescence of said barrier wall.

28. The system of claim 1 wherein said radiation detecting means comprises a probe having a handle portion and a needle portion, said needle portion being removably mounted on said handle portion.

29. The system of claim 28 wherein said radiation detecting means comprises a radiation sensor located in said needle portion.

30. A system for detecting and destroying living tumor tissue within the body of a living being, said system comprising a tumor localizing radiopharmaceutical, a small diameter tissue-penetratable radiation detecting means, and tumor destroying means, said tumor localizing radiopharmaceutical being attached to the living tumor tissue, whereupon said radiopharmaceutical produces tumor-localizing radiation from the living tumor tissue, said small diameter tissue-penetratable radiation detecting means being arranged to be inserted into the body of the being with minimal invasion of the being via a percutaneous incision or access port into the tumor tissue and being movable along a path within the tumor tissue for location at various positions therein for detecting said tumor localizing radiation from a plurality of directions and for providing a signal indicative of the three dimensional distribution of the living tumor tissue to which said radiopharmaceutical is attached, said tumor destroying means being arranged to be inserted into the body of said being into said living tumor tissue for destroying said living tumor tissue from within it.

31. The system of claim 30 wherein said tumor destroying means includes means for carrying pieces of destroyed tumor tissue out of the body of the being for determination of the existence of radioactivity therein.

32. The system of claim 30 wherein said tumor-localizing radiation comprises photons of different energies, including gamma radiation, X radiation and/or annihilation radiation produced by said radiopharmaceutical, wherein said radiation detecting means is arranged to detect said photons, and wherein system comprises analyzing means utilizing the known naturally occurring abundance of emitted photons of different energies of said radiopharmaceutical as a reference factor to provide said indication of the three dimensional distribution of the living tumor tissue to which said radiopharmaceutical is attached.

33. The system of claim 31 wherein said tumor-localizing radiation comprises photons of different energies produced by said radiopharmaceutical, wherein said radiation detecting means is arranged to detect said photons, and wherein system comprises analyzing means utilizing the known naturally occurring abundance of emitted photons of different energies of said radiopharmaceutical as a reference factor to provide said indication of the three dimensional distribution of the living tumor tissue to which said radiopharmaceutical is attached.

34. The system of claim 32 wherein said photons of different energies comprise characteristic x-ray photons and full energy gamma-ray photons of a known ratio to each other, and wherein said analyzing means compares said known ratio to the ratio of the photons of said characteristic x-ray photons detected to said full energy gamma-ray photons detected.

35. The system of claim 33 wherein said photons of different energies comprise characteristic x-ray photons and full energy gamma-ray photons of a known ratio to each other, and wherein said analyzing means compares said known ratio to the ratio of the photons of said characteristic x-ray photons detected to said full energy gamma-ray photons detected.

36. The system of claim 30 wherein said radiation detecting means comprises an elongated, small diameter probe suitable for percutaneous insertion into the body of the being and having a radiation sensor therein.

37. The system of claim 36 wherein said tumor destroying means comprises an elongated, small diameter instrument suitable for percutaneous insertion into the body of the being.

38. The system of claim 37 additionally comprising an elongated lumen suitable for percutaneous insertion into the body of the being and arranged to have said probe inserted therethrough into said living tumor tissue to detect said tumor localizing radiation to provide said signal, said probe being removable from said lumen, said instrument being arranged to be inserted through said lumen to destroy said living tumor tissue from within said living tumor tissue.

39. The system of claim 38 wherein said probe includes a longitudinal axis and wherein said probe is arranged to be moved to various positions along said axis to position said sensor at various positions within said living tumor tissue.

40. The system of claim 39 wherein said probe is arranged to be rotated to various angular positions about said axis at any of said various positions of said sensor.

41. The system of claim 36 wherein said radiation detecting means comprises a radiation sensor selected from the group consisting of a scintillation crystal and a solid state semi-conductor detector.

42. The system of claim 36 wherein said probe comprises a handle and a needle releasably mounted thereto, and wherein said sensor is mounted in said needle.

43. The system of claim 36 wherein said sensor has a predetermined field of view.

44. The system of claim 43 wherein said probe includes collimation means for limiting said predetermined field of view.

45. The system of claim 36 wherein said probe additionally comprises radiation detection enhancing means comprising a barrier wall disposed adjacent said sensor for blocking radiation to said sensor from various directions, said barrier wall having an opening through which radiation may pass for reflection from said barrier wall to said sensor.

46. The system of claim 45 wherein said barrier wall is ovate in shape and wherein said opening is at one end thereof.

47. The system of claim 45 wherein said barrier wall is formed of a material which fluoresces to produce x-rays when exposed to radiation from said living tumor tissue, and wherein said barrier wall is disposed so that said sensor receives the x-rays produced by the fluorescence of said barrier wall.

48. The system of claim 36 wherein said probe is disposable.

49. The system of claim 36 wherein said tumor-localizing radiation comprises photons of different energies produced by said radiopharmaceutical, wherein said radiation detecting means is arranged to detect said photons, and wherein system comprises analyzing means utilizing the known naturally occurring abundance of emitted photons of different energies of said radiopharmaceutical to provide said indication of the three dimensional distribution of the living tumor tissue to which said radiopharmaceutical is attached and wherein said probe is disposable and said analyzer is suitable for reuse.

50. A probe for detecting radiation from living tumor tissue tagged with a radiopharmaceutical within the body of a living being, the radiopharmaceutical producing tumor-localizing radiation from the living tumor tissue, said probe being an elongated member comprising a radiation sensor and radiation detection enhancing means, said probe being arranged to be inserted into the body of the being adjacent the tumor tissue for detecting said tumor localizing radiation from a plurality of directions and for providing a signal indicative of the three dimensional distribution of the living tumor tissue to which said radiopharmaceutical is attached, said radiation detection enhancing means comprising a hollow member including barrier wall defining a hollow interior, said barrier wall being disposed adjacent said sensor for blocking radiation to said sensor from various directions, said barrier wall having an opening in communication with said hollow interior through which radiation may pass whereupon the radiation is reflected from said barrier wall to said sensor.

51. The probe of claim 50 wherein said barrier wall is ovate in shape and wherein said opening is at one end thereof.

52. The probe of claim 50 wherein said barrier wall is formed of a material which fluoresces to produce x-rays when exposed to radiation from said living tumor tissue, and wherein said barrier wall is disposed so that said sensor receives the x-rays produced by the fluorescence of said barrier wall.

53. The probe of claim 51 wherein said barrier wall is formed of a material which fluoresces to produce x-rays when exposed to radiation from said living tumor tissue, and wherein said barrier wall is disposed so that said sensor receives the x-rays produced by the fluorescence of said barrier wall.

54. The probe of claim 50 wherein said sensor is selected from the group consisting of a scintillation crystal and a solid state semi-conductor detector.

55. The probe of claim 50 wherein said probe comprises a needle having a sharp tip.

56. The probe of claim 50 wherein said probe comprises a handle and a needle releasably secured thereto, said sensor being located in said needle.

57. A method for determining the three dimensional representation of living tumor tissue within the body of a living being, said method comprising:
(a) providing a tumor localizing radiopharmaceutical, said tumor localizing radiopharmaceutical being attached to the living tumor tissue, whereupon said radiopharmaceutical produces tumor-localizing radiation from the living tumor tissue;
(b) providing a small diameter penetratable radiation detecting means;
(c) inserting said small diameter penetratable radiation detecting means into the body of the being with minimal invasion of the being percutaneously;
(d) moving said small diameter penetratable radiation detecting means along a path within the living tumor tissue for location at various positions within the living tumor tissue; and
(e) detecting said tumor localizing radiation from a plurality of directions therein to provide an indication of the three dimensional distribution of the living tumor tissue to which said radiopharmaceutical is attached and for providing a signal indicative thereof.

58. The method of claim 57 wherein said tumor-localizing radiation comprises photons of different energies including gamma radiation, X radiation and/or annihilation radiation produced by said radiopharmaceutical and wherein said signal is provided by using the known naturally occurring abundance of emitted photons of different energies of said radiopharmaceutical.

59. The method of claim 58 wherein said photons of different energies comprise characteristic x-ray photons and full energy gamma-ray photons of a known ratio to each other, and wherein said method comprises comparing said known ratio to the ratio of the photons of said characteristic x-ray photons detected to said full energy gamma-ray photons detected.

60. The method of claim 59 wherein said penetratable radiation detecting means is an elongated probe suitable for percutaneous introduction into the body of the being, and wherein said probe is introduced percutaneously into the body of the being.

61. The method of claim 60 wherein said probe has a longitudinal axis, and wherein said method comprises moving said probe along said axis and/or rotating said probe about said longitudinal axis within the living tumor tissue for detecting said tumor localizing radiation.

62. The method of claim 57 additionally comprising the step of destroying said living tumor tissue from within said living tumor tissue by introducing tumor destroying means therein.

63. The method of claim 57 additionally comprising the step of destroying said living tumor tissue from within said living tumor tissue by introducing tumor destroying means therein.

64. The method of claim 63 wherein said tumor destroying means comprises a dose of a necrotizing agent.

65. The method of claim 64 wherein said necrotizing agent is radioactive.

66. The method of claim 65 wherein said radioactive agent provides an emission selected from the group consisting of alpha rays, beta rays, gamma rays, x rays, and neutrons and wherein said emission is applied to the living tumor tissue.

67. The method of claim 64 wherein said necrotizing agent comprises a pharmacologic substance.

68. The method of claim 64 wherein said necrotizing agent comprises ultrasonic waves.

69. The method of claim 64 wherein said necrotizing agent comprises a laser beam.

70. The method of claim 64 wherein said necrotizing agent is thermal.

71. The method of claim 70 wherein said thermal agent necrotizes the living tumor tissue by heating it.

72. The method of claim 70 wherein said thermal agent necrotizes the living tumor tissue by cooling it.

73. A method for determining the three dimensional representation of living tumor tissue within the body of a living being, said method comprising:
(a) providing a tumor localizing radiopharmaceutical, said tumor localizing radiopharmaceutical being attached to the living tumor tissue, whereupon said radiopharmaceutical produces tumor-localizing radiation from the living tumor tissue, said tumor-localizing radiation comprising photons of different energies produced by said radiopharmaceutical;
(b) providing a small diameter penetratable radiation detecting means;
(c) inserting said small diameter penetratable radiation detecting means into the body of the being with minimal invasion of the being percutaneously;
(d) moving said small diameter penetratable radiation detecting means along a path within the living tumor tissue for location at various positions within the living tumor tissue; and
(e) detecting said tumor localizing radiation from a plurality of directions to provide an indication of the three dimensional distribution of the living tumor tissue to which said radiopharmaceutical is attached and for providing a signal indicative thereof.

74. The method of claim 73 wherein said penetratable radiation detecting means is an elongated device having a longitudinal axis, and wherein said penetratable radiation detecting means is caused to be rotated about said longitudinal axis within the living tumor tissue for detecting said tumor localizing radiation.

75. The method of claim 74 wherein said penetratable radiation detecting means is moved into the living tumor tissue along a path parallel to said longitudinal axis.

76. The method of claim 73 additionally comprising the step of providing a dose of a necrotizing agent to the living tumor tissue.

77. The method of claim 76 wherein said necrotizing agent is radioactive.

78. The method of claim 77 wherein said radioactive agent provides an emission selected from the group consisting of alpha rays, beta rays, gamma rays, x rays, and neutrons and wherein said emission is applied to the living tumor tissue.

79. The method of claim 73 wherein said method additionally comprises utilizing the known naturally occurring abundance of emitted photons of different energies of said radiopharmaceutical as a reference factor.

80. The method of claim 78 wherein said emission is a radiation therapy beam provided from either inside or outside of the body of the being.

81. The method of claim 76 wherein said necrotizing agent comprises a pharmacologic substance.

82. The method of claim 81 wherein said pharmacologic substance comprises one or more of the group comprising metal powders and colloids of iron and copper.

83. The method of claim 76 wherein said necrotizing agent comprises ultrasonic waves.

84. The method of claim 83 wherein said ultrasonic waves are provided from either outside or inside of the body of the being.

85. The method of claim 76 wherein said necrotizing agent comprises a laser beam.

86. The method of claim 85 wherein said laser beam is provided from either outside or inside of the body of the being.

87. The method of claim 76 wherein said necrotizing agent is thermal.

88. The method of claim 87 wherein said thermal agent necrotizes the living tumor tissue by the heating it.

89. The method of claim 87 wherein said thermal agent necrotizes the living tumor tissue by cooling it.

90. The method of claim 87 wherein said thermal agent is provided from either outside or inside of the body of the being.

91. The method of claim 73 additionally comprising the step of removing at least a portion of the living tumor tissue from the body of the being.

92. The method of claim 91 wherein the removal of the living tumor tissue from the body of the being is accomplished continuously.

93. The method of claim 91 additionally comprising the step of examining the removed tissue for radioactivity.

* * * * *

REEXAMINATION CERTIFICATE (4224th)

United States Patent
Carroll et al.

[19]

[11] B1 5,846,513
[45] Certificate Issued  Nov. 28, 2000

[54] TUMOR LOCALIZATION AND REMOVAL SYSTEM USING PENETRATABLE DETECTION PROBE AND REMOVAL INSTRUMENT

[75] Inventors: Robert G. Carroll, Largo, Fla.; Robin A. Wise, Jr., Morgan Hill, Calif.

[73] Assignee: Carewise Medical Products Corporation, Morgan Hill, Calif.

Reexamination Request:
No. 90/005,247, Feb. 4, 1999

Reexamination Certificate for:
Patent No.: 5,846,513
Issued: Dec. 8, 1998
Appl. No.: 08/889,469
Filed: Jul. 8, 1997

[51] Int. Cl.[7] .............................. G01T 1/166; A61B 6/00; A61K 51/00
[52] U.S. Cl. ..................... 424/111; 424/9.1; 250/336.1; 250/363.1; 250/370.01; 128/659
[58] Field of Search ................ 424/111, 9.1; 250/336.1, 250/363.1, 370.01; 128/659

[56] References Cited

U.S. PATENT DOCUMENTS 4,995,396  2/1991  Inaba et al. .
5,014,708  5/1991  Hayashi et al. .
5,694,933  12/1997  Madden et al. .

FOREIGN PATENT DOCUMENTS

WO 94/03108  2/1994  WIPO .

OTHER PUBLICATIONS

Wong et al., Int. J. Radiation Oncology Biol. Phys. vol. 14, pp. 353–359, 1988.

*Primary Examiner*—Yvonne Eyler

[57] ABSTRACT

A system for detecting and destroying living tumor tissue within the body of a living being. The system is arranged to be used with a tumor localizing radiopharmaceutical. The system includes a percutaneously insertable radiation detecting probe, an associated analyzer, and a percutaneously insertable tumor removing instrument, e.g., a resectoscope. The radiation detecting probe includes a needle unit having a radiation sensor component therein and a handle to which the needle unit is releasably mounted. The needle is arranged to be inserted through a small percutaneous portal into the patient's body and is movable to various positions within the suspected tumor to detect the presence of radiation indicative of cancerous tissue. The probe can then be removed and the tumor removing instrument inserted through the portal to destroy and/or remove the cancerous tissue. The instrument not only destroys the tagged tissue, but also removes it from the body of the being so that it can be assayed for radiation to confirm that the removed tissue is cancerous and not healthy tissue. A collimator may be used with the probe to establish the probe's field of view.

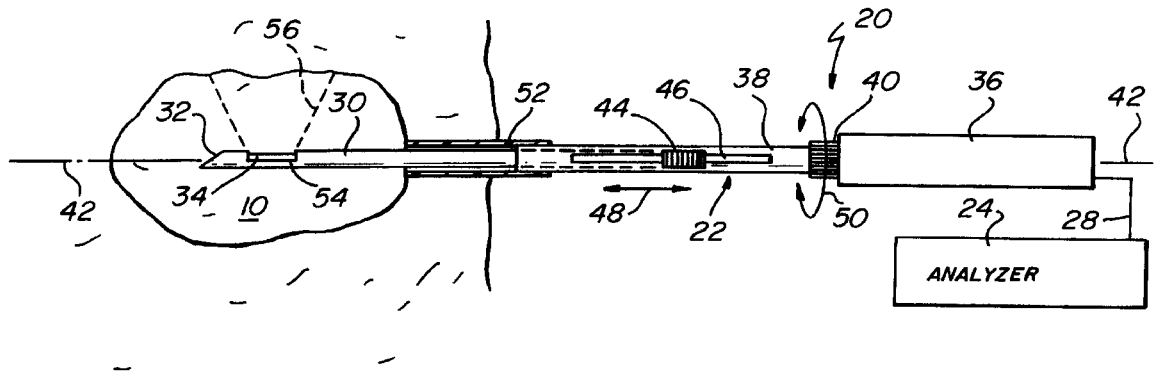

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–93 is confirmed.

New claims 94–140 are added and determined to be patentable.

94. *A system for determining the three dimensional representation of living tumor tissue within the body of a living being, said system comprising a tumor localizing radiopharmaceutical and small diameter penetratable radiation detecting means in the form of a hollow needle having a sharp tip, said tumor localizing radiopharmaceutical being attached to the living tumor tissue, whereupon said radiopharmaceutical produces tumor-localizing radiation from the living tumor tissue, said tumor-localizing radiation comprising photons of different energies produced by said radiopharmaceutical, said small diameter penetratable radiation detecting means being arranged to be inserted into the body of the being with minimal invasion of the being via a percutaneous incision or access port and being movable along a path within the tumor tissue for location at various positions within the tumor tissue for detecting said tumor localizing radiation from a plurality of directions therein to provide an indication of the three dimensional distribution of the living tumor tissue to which said radiopharmaceutical is attached and for providing a signal indicative thereof.*

95. *The system of claim 94 wherein said penetratable radiation detecting means is an elongated member having a longitudinal axis, and is arranged to penetrate the tumor tissue and be rotated about said longitudinal axis to various angular positions.*

96. *The system of claim 94 additionally comprising tumor tissue destroying means for destroying the living tumor tissue.*

97. *The system of claim 96 wherein said tissue destroying means is arranged for providing a dose of a necrotizing agent therefrom.*

98. *The system of claim 97, wherein said necrotizing agent comprises a radioactive agent.*

99. *The system of claim 98 wherein said radioactive agent is in a locally persistent form arranged for location adjacent the situs of the living tumor tissue, whereupon said radioactive agent produces radiation emissions therefrom to necrotize the living tumor tissue.*

100. *The system of claim 98 wherein said radioactive agent produces emissions of one or more of the group comprising alpha rays, beta rays, gamma rays, x rays, and neutrons, and wherein said necrotizing means provides said emissions to the living tumor tissue.*

101. *The system of claim 97 wherein said necrotizing agent comprises a pharmacologic substance.*

102. *The system of claim 97 wherein said necrotizing agent comprises ultrasonic waves, and wherein said necrotizing means provides said ultrasonic waves to the living tumor tissue.*

103. *The system of claim 97 wherein said necrotizing agent comprises a laser beam, and wherein said necrotizing means provides said laser beam to the living tumor tissue.*

104. *The system of claim 97 wherein said necrotizing agent is thermal, and wherein said necrotizing means provides said thermal agent to the living tumor tissue.*

105. *The system of claim 95 additionally comprising means for removing at least a portion of the living tumor tissue from the body of the living being.*

106. *The system of claim 105 wherein said means for removing operates on a continuing basis.*

107. *The system of claim 105 additionally comprising means for determining if said removed portion of the living tumor tissue is radioactive.*

108. *The system of claim 95 wherein said penetratable radiation detecting means has a longitudinal axis and comprises a sensor having a predetermined field of view for detecting radiation with said field of view.*

109. *The system of claim 108 wherein said field of view extends laterally of said longitudinal axis.*

110. *The system of claim 108 additionally comprising collimator means for limiting said field of view.*

111. *The system of claim 108 additionally comprising radiation detection enhancing means comprising a barrier wall disposed adjacent said sensor for blocking radiation to said sensor from various directions, said barrier wall having an opening through which radiation may pass for reflection from said barrier wall to said sensor.*

112. *The system of claim 111 wherein said barrier wall is ovate in shape and wherein said opening is at one end thereof.*

113. *The system of claim 111 wherein said barrier wall is formed of a material which fluoresces to produce x-rays when exposed to radiation from said living tumor tissue, and wherein said barrier wall is disposed so that said sensor receives the x-rays produced by the fluorescence of said barrier wall.*

114. *The system of claim 94 wherein said radiation detecting means comprises a probe having a handle portion and said needle, said needle being removably mounted on said handle portion.*

115. *The system of claim 114 wherein said radiation detecting means comprises a radiation sensor located in said needle.*

116. *The system of claim 95 wherein said tumor destroying means includes means for carrying pieces of destroyed tumor tissue out of the body of the being for determination of the existence of radioactivity therein.*

117. *The system of claim 95 wherein said tumor-localizing radiation comprises photons of different energies, including gamma radiation, X radiation and/or annihilation radiation produced by said radiopharmaceutical, wherein said radiation detecting means is arranged to detect said photons, and wherein system comprises analyzing means utilizing the known naturally occurring abundance of emitted photons of different energies of said radiopharmaceutical as a reference factor to provide said indication of the three dimensional distribution of the living tumor tissue to which said radiopharmaceutical is attached.*

118. *The system of claim 116 wherein said tumor-localizing radiation comprises photons of different energies produced by said radiopharmaceutical, wherein said radiation detecting means is arranged to detect said photons, and wherein system comprises analyzing means utilizing the known naturally occurring abundance of emitted photons of different energies of said radiopharmaceutical as a reference factor to provide said indication of the three dimen-* sional distribution of the living tumor tissue to which said radiopharmaceutical is attached.

119. The system of claim 117 wherein said photons of different energies comprise characteristic x-ray photons and full energy gamma-ray photons of a known ratio to each other, and wherein said analyzing means compares said known ratio to the ratio of the photons of said characteristic x-ray photons detected to said full energy gamma-ray photons detected.

120. The system of claim 118 wherein said photons of different energies comprise characteristic x-ray photons and full energy gamma-ray photons of a known ratio to each other, and wherein said analyzing means compares said known ratio to the ratio of the photons of said characteristic x-ray photons detected to said full energy gamma-ray photons detected.

121. The system of claim 95 additionally comprising an elongated lumen suitable for percutaneous insertion into the body of the being and arranged to have said needle inserted therethrough into said living tumor tissue to detect said tumor localizing radiation to provide said signal, said needle being removable from said lumen.

122. The system of claim 121 additionally comprising an instrument being arranged to be inserted through said lumen to destroy said living tumor tissue from within said living tumor tissue.

123. The system of claim 94 wherein said needle forms a portion of a probe, said probe additionally comprising a radiation sensor and radiation detection enhancing means, said radiation detection enhancing means comprising a hollow member including barrier wall defining a hollow interior, said barrier wall being disposed adjacent said sensor for blocking radiation to said sensor from various directions, said barrier wall having an opening in communication with said hollow interior through which radiation may pass, whereupon the radiation is reflected from said barrier wall to said sensor.

124. The system of claim 123 wherein said barrier wall is ovate in shape and wherein said opening is at one end thereof.

125. The system of claim 123 wherein said barrier wall is formed of a material which fluoresces to produce x-rays when exposed to radiation from said living tumor tissue, and wherein said barrier wall is disposed so that said sensor receives the x-rays produced by the fluorescence of said barrier wall.

126. The system of claim 124 wherein said barrier wall is formed of a material which fluoresces to produce x-rays when exposed to radiation from said living tumor tissue, and wherein said barrier wall is disposed so that said sensor receives the x-rays produced by the fluorescence of said barrier wall.

127. The system of claim 123 wherein said sensor is selected from the group consisting of a scintillation crystal and a solid state semi-conductor detector.

128. A method for determining the three dimensional representation of living tumor tissue within the body of a living being, said method comprising:

(a) providing a tumor localizing radiopharmaceutical, said tumor localizing radiopharmaceutical being attached to the living tumor tissue, whereupon said radiopharmaceutical produces tumor-localizing radiation from the living tumor tissue, said tumor-localizing radiation comprising photons of different energies produced by said radiopharmaceutical;

(b) providing a small diameter penetratable radiation detecting probe including a hollow needle having a sharp tip;

(c) inserting said small diameter penetratable radiation detecting probe into the body of the being with minimal invasion of the being percutaneously;

(d) moving said small diameter penetratable radiation detecting probe along a path within the living tumor tissue for location at various positions within the living tumor tissue; and (e) detecting said tumor localizing radiation from a plurality of directions therein to provide an indication of the three dimensional distribution of the living tumor tissue to which said radiopharmaceutical is attached and for providing a signal indicative thereof.

129. The method of claim 128 wherein said tumor-localizing radiation comprises photons of different energies including gamma radiation, X radiation and/or annihilation radiation produced by said radiopharmaceutical and wherein said signal is provided by using the known naturally occurring abundance of emitted photons of different energies of said radiopharmaceutical.

130. The method of claim 129 wherein said photons of different energies comprise characteristic x-ray photons and full energy gamma-ray photons of a known ratio to each other, and wherein said method comprises comparing said known ratio to the ratio of the photons of said characteristic x-ray photons detected to said full energy gamma-ray photons detected.

131. The method of claim 128 wherein said probe suitable for percutaneous introduction into the body of the being, and wherein said probe is introduced percutaneously into the body of the being.

132. The method of claim 128 wherein said probe has a longitudinal axis, and wherein said method comprises moving said probe along said axis and/or rotating said probe about said longitudinal axis within the living tumor tissue for detecting said tumor localizing radiation.

133. The method of claim 128 additionally comprising the step of destroying said living tumor tissue from within said living tumor tissue by introducing tumor destroying means therein.

134. The method of claim 133 wherein said tumor destroying means comprises a dose of a necrotizing agent.

135. The method of claim 134 wherein said necrotizing agent is radioactive.

136. The method of claim 135 wherein said radioactive agent provides an emission of one or more of the group comprising alpha rays, beta rays, gamma rays, x rays, and neutrons and wherein said emission is applied to the living tumor tissue.

137. The method of claim 134 wherein said necrotizing agent comprises a pharmacologic substance.

138. The method of claim 134 wherein said necrotizing agent comprises ultrasonic waves.

139. The method of claim 134 wherein said necrotizing agent comprises a laser beam.

140. The method of claim 134 wherein said necrotizing agent is thermal.

* * * * *